US008686185B2

(12) United States Patent
Gwag et al.

(10) Patent No.: US 8,686,185 B2
(45) Date of Patent: Apr. 1, 2014

(54) MANUFACTURING METHOD OF 2-HYDROXY-5-PHENYLALKYLAMINOBENZOIC ACID DERIVATIVES AND THEIR SALTS

(75) Inventors: Byoung Joo Gwag, Suwon-si (KR); Jae Young Cho, Suwon-si (KR); Young Ae Lee, Suwon-si (KR); Cheng Qiling, Dongyang (CN); Yulian Wu, Dongyang (CN); Li Xing, Dongyang (CN)

(73) Assignee: Neurotech Pharmaceuticals Co., Ltd., Suwon-si (KR)

(*) Notice: Subject to any disclaimer, the term of this patent is extended or adjusted under 35 U.S.C. 154(b) by 0 days.

(21) Appl. No.: 12/742,217

(22) PCT Filed: Oct. 30, 2008

(86) PCT No.: PCT/KR2008/006432
§ 371 (c)(1),
(2), (4) Date: Sep. 20, 2010

(87) PCT Pub. No.: WO2009/064084
PCT Pub. Date: May 22, 2009

(65) Prior Publication Data
US 2011/0028757 A1    Feb. 3, 2011

(30) Foreign Application Priority Data

Nov. 12, 2007  (KR) .................. 10-2007-0114660

(51) Int. Cl.
*C07C 229/64* (2006.01)
(52) U.S. Cl.
USPC ................................ 562/458; 560/47
(58) Field of Classification Search
CPC .................................................. C07C 227/18
USPC .......................................... 560/48, 47, 458
See application file for complete search history.

(56) References Cited

U.S. PATENT DOCUMENTS

| 3,632,760 | A | 1/1972 | Shen et al. | 514/166 |
| 3,674,844 | A | 7/1972 | Shen et al. | 562/440 |
| 4,753,964 | A | 6/1988 | Horrobin | 514/558 |
| 5,434,163 | A | 7/1995 | Edlind et al. | 514/310 |
| 5,527,814 | A | 6/1996 | Louvel | 514/367 |
| 5,762,922 | A | 6/1998 | Noble et al. | 424/85.4 |
| 6,136,835 | A | 10/2000 | Camden | 514/383 |
| 6,358,945 | B1 | 3/2002 | Breitfelder et al. | 514/227 |
| 6,573,402 | B1 | 6/2003 | Gwag et al. | 562/435 |
| 6,927,303 | B2 | 8/2005 | Gwag et al. | 560/136 |
| 6,964,982 | B2 | 11/2005 | Gwag et al. | 514/535 |
| 7,189,878 | B2 | 3/2007 | Gwag et al. | 564/373 |
| 7,319,160 | B2 | 1/2008 | Gwag et al. | 560/47 |
| 7,371,896 | B2 | 5/2008 | Gwag et al. | 562/457 |
| 7,511,074 | B2 | 3/2009 | Gwag et al. | 514/535 |
| 7,608,585 | B2 | 10/2009 | Gwag et al. | 514/12 |
| 7,750,045 | B2 | 7/2010 | Gwag et al. | 514/535 |
| 2006/0235239 | A1* | 10/2006 | Gwag et al. | 560/37 |

FOREIGN PATENT DOCUMENTS

| DE | 2031227 | 1/1971 |
| EP | 122827 A1 | 10/1984 |
| GB | 1268465 | 3/1972 |
| JP | 54-125632 | 9/1979 |
| JP | 2000-212141 | 8/2000 |
| JP | 2000-273041 | 10/2000 |
| KR | 2003-058934 | 7/2003 |
| WO | WO 86/03199 | 6/1986 |
| WO | WO 94/13663 | 6/1994 |
| WO | WO 95/22342 | 8/1995 |
| WO | WO 99/01421 | 1/1999 |
| WO | WO 01/79153 | 10/2001 |

OTHER PUBLICATIONS

Solomons, Organic Chemistry, 5th Edition, 1992, Jon Wiley &Sons, Inc., New York, pp. 240-243.*

* cited by examiner

*Primary Examiner* — Paul A Zucker
(74) *Attorney, Agent, or Firm* — Seed IP Law Group PLLC

(57) ABSTRACT

The present invention provides an efficient method for mass-producing 2-hydroxy-5-(substituted)phenylalkylamino benzoic acid derivatives represented by specific Chemical formulas or their salts, particularly 2-hydroxy-5-[2-(4-trifluoromethylphenyl)ethylamino]benzoic acid or its salt.

8 Claims, No Drawings

MANUFACTURING METHOD OF 2-HYDROXY-5-PHENYLALKYLAMINOBENZOIC ACID DERIVATIVES AND THEIR SALTS

TECHNICAL FIELD

The present invention relates to manufacturing method of 2-hydroxy-5-(substituted)phenylalkylaminobenzoic acid derivatives and their salts.

BACKGROUND ART 2-hydroxy-5-(substituted)phenylalkylaminobenzoic acid derivatives, particularly 2-hydroxy-5-[2-(4-trifluoromethyl phenyl)ethylamino]benzoic acid and its salt, are known to be very useful for treating central nervous system (CNS) diseases such as ischemia, hypoxia, hypoglycemia, traumatic brain injury, traumatic spinal cord injury, epilepsy, Huntington's disease, Parkinson's disease, Alzheimer's disease and amyotrophic lateral sclerosis (U.S. Pat. No. 6,964,982).

As a synthesis method of the 2-hydroxy-5-(substituted)phenylalkylaminobenzoic acid, a preparing method of 2-hydroxy-5-phenylalkylaminobenzoic acid using substitution reaction mechanism performed by reacting aminosalicylic acid and 2-(4-nitrophenyl)ethylbromide or 3-(4-nitrophenyl)propylbromide in a mixture of triethylamine and dimethylformamide (Korean patent laid-open publication No. 2003-0058934).

However, in case of using said method, the intended substitution reaction is unlikely to happen because the amine residue of aminosalicylic acid works as base, and a specific residue of starting material, 2-(4-nitrophenyl)ethylbromide or is likely to be removed as hydrogen bromide, which causes formation of impurities, 4-nitrostyrene or 1-allyl-4-nitrobenzene. In addition, these impurities are difficult to be removed by general recrystallization method.

In addition to the above method, other methods have been disclosed, but all methods disclosed until now have problem that those are not suitable for mass-production.

DISCLOSURE

Technical Problem

Accordingly, the object of the present invention is to provide a method useful in mass-producing 2-hydroxy-5-phenylalkylaminobenzoic acid derivative or its salt

Technical Solution

To achieve the object, the present invention provides a method for preparing 2-hydroxy-5-phenylalkylaminobenzoic acid derivative represented by Chemical formula 4 or its salt, comprising a step of preparing alkyl 2-hydroxy-5-phenylalkylaminobenzoate represented by Chemical formula 3 by reacting phenylalkyl methanesulfonate represented by Chemical formula 1 with alkyl 5-aminosalicylate represented by Chemical formula 2.

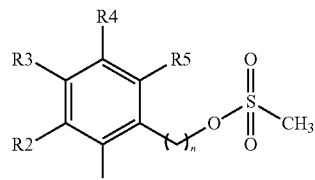

<Chemical formula 1>

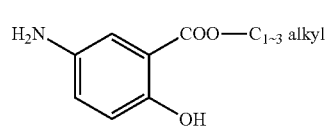

<Chemical formula 2>

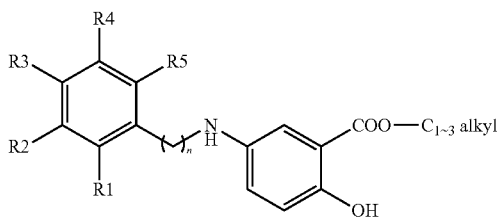

<Chemical formula 3>

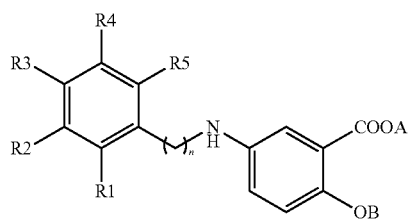

<Chemical formula 4>

In the Chemical formulas 1 to 4, n is an integer from 1 to 4; R1, R2, R3, R4 and R5 are independently hydrogen, halogen, $C_{1\sim4}$ haloalkyl, nitro, hydroxy, $C_{1\sim4}$ alkyl, aryl, $C_{1\sim4}$ alkoxy or amine; A is hydrogen or $C_{1\sim3}$ alkyl; and B is hydrogen or acetyl.

Preferably, the present invention is the method wherein the reaction temperature of phenylalkyl methanesulfonate represented by Chemical formula 1 and alkyl 5-aminosalicylate represented by Chemical formula 2 is 60-90° C. More preferably, the reaction temperature of the Chemical formula 1 compound and the Chemical formula 2 compound is 70-80° C.

Higher temperature than the range of the present invention accelerates not only the main reaction, but also the side reactions more significantly, which therefore introduces more impurities and lowers the yield. Lower temperature than the range of the present invention reduces reaction speed, which requires too much manufacturing time.

Preferably, the present invention also provides the method wherein the method comprises hydrolyzing alkyl 2-hydroxy-5-(substituted)phenylalkylaminobenzoate represented by Chemical formula 3 in a solvent comprising sulphuric acid water solution to form 2-hydroxy-5-(substituted)phenylalkylaminobenzoic acid sulfate.

The present invention also provides the method wherein the method comprises controlling the pH of the 2-hydroxy-5-(substituted)phenylalkylaminobenzoic acid sulfate to pH 3~3.5 to make 2-hydroxy-5-(substituted)phenylalkylaminobenzoic acid non-solvate, particularly, 2-hydroxy-5-[2-(4-trifluoromethylphenyl)ethylamino]benzoic acid non-solvate. The obtained 2-hydroxy-5-(substituted)phenylalkylaminobenzoic acid sulfate, particularly, 2-hydroxy-5-[2-(4-trifluoromethylphenyl)ethylamino]benzoic acid sulfate, has both amino group and carboxyl group, and it can react with strong acid to form ammonium and react with alkali to form carboxylate in the outside of the pH range, which makes a bad effect on the purity of the final product.

The 2-hydroxy-5-(substituted)phenylalkylaminobenzoic acid derivative represented by Chemical formula 4 can be made by using the 2-hydroxy-5-(substituted)phenylalkylaminobenzoic acid as starting material, and purifying alkyl 2-hydroxy-5-(substituted)phenylalkylaminobenzoate of Chemical formula 3 without further reaction.

Salts of the 2-hydroxy-5-(substituted)phenylalkylaminobenzoic acid derivative represented by Chemical formula 4, particularly 2-hydroxy-5-(substituted)phenylalkylaminobenzoic acid (both A and B are hydrogen in Chemical formula 4), can be made by reacting the compound with inorganic reagent providing alkali metal like lithium hydroxide, sodium hydroxide, potassium hydroxide and so on in organic solvent such as lower alcohol, acetone and acetonitrile. Amine salts can be made by dissolving the Chemical formula 4 compound in alcohol solvent and adding diethylamine, triethylamine etc. to the solution. However, the method for preparing the salt of the present invention is not limited to those methods described above. Metal salt can be obtained by direct crystallization method, and freeze drying method can be used to get the salt of Chemical formula 4 compound.

MODES FOR CARRYING OUT THE INVENTION

Hereinafter, the present invention is described in considerable detail to help those skilled in the art understand the present invention. However, the following examples are offered by way of illustration and are not intended to limit the scope of the invention. It is apparent that various changes may be made without departing from the spirit and scope of the invention or sacrificing all of its material advantages.

Example

Preparation of 2-hydroxy-5-[2-(4-trifluoromethylphenyl)ethylamino]benzoic acid 2-hydroxy-5-[2-(4-trifluoromethylphenyl)ethylamino] benzoic acid represented by Chemical formula 8 was prepared according to a step of preparing methyl 2-hydroxy-5-[2-(4-trifluoromethylphenyl)ethylamino]benzoate represented by Chemical formula 7 by reacting 2-(4-trifluoromethylphenyl)ethyl methanesulfonate represented by Chemical formula 5 with methyl 5-aminosalicylate represented by Chemical formula 6:

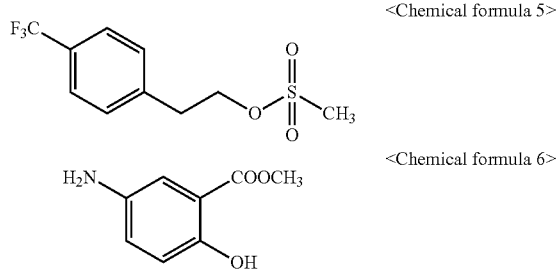

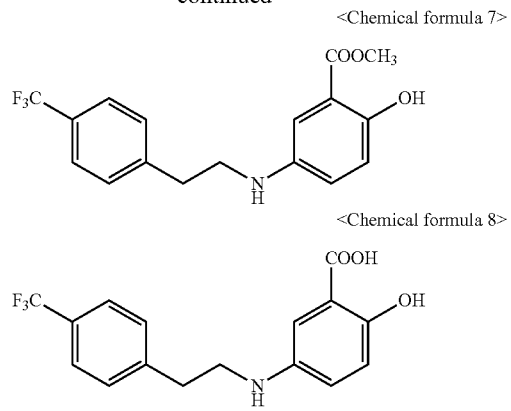

Step I: Condensation

Into a 50 L glass reactor, 7.00 kg of methyl 5-aminosalicylate (41.9 mol), 11.23 kg of compound A (2-(4-trifluoromethylphenyl)ethyl methanesulfonate, 41.9 mol), 5.11 kg of triethylamine (50.6 mol) and 26 L of toluene were charged under nitrogen protection. The mixture were agitated and heated to about 70-80° C. to react for about 28-32 hours. After 20 hours' reaction, samples were taken every 4 hours for HPLC analysis. The reaction was considered complete when compound A was not more than 0.5%. The reaction mixture was then cooled to 45° C., then transferred to a 20 L rotary evaporator and concentrated under about 0.09 MPa vacuum at 60-75° C. until no toluene was condensed. A dark oily product (22.31 kg) was obtained, which was dissolved in ethanol and acidified with 50% sulfuric acid. The mixture was cooled to below 10° C. for sufficient precipitation. After filtered and sufficiently washed with 50% ethanol, 13.99 kg wet sulfate of compound B (methyl 2-hydroxy-5-[2-(4-trifluoromethylphenyl)ethylamino]benzoate) was obtained (74.8% on dry base, 90.73% HPLC purity). The yield was 58.4%.

Step II: Hydrolyzation

Under nitrogen protection, 11.6 kg of the sulfate obtained in Step I (9.04 kg on dry base, 21.1 mol) was hydrolyzed in the mixture of 13.2 kg of 98% sulfuric acid (132 mol), 36 L of purified water and 8.2 kg of acetic acid (136.7 mol) at 95~100° C. for about 27 hours. Samples were taken for HPLC analysis. The reaction was considered complete when the residue of compound B was not more than 1%. Then the reaction mixture was cooled to 10-20° C. and filtered. The cake was washed with 6 L of purified water for three times and 10.98 kg of wet sulfate of compound C (2-hydroxy-5-[2-(4-trifluoromethylphenyl)ethylamino]benzoic acid) was obtained (69.4% on dry base, 97.67% HPLC purity). The yield was 94.2%.

Step III: Purification

The mixture of 10.94 kg of the sulfate of compound C obtained in step II, 30 L of anhydrous ethanol and 7.5 L of purified water was heated to 50~65° C. with agitation, then 50% sulfuric acid solution was added dropwise until a clear solution was obtained. The solution was filtered and gradually cooled down to below 10° C. After filtration, 8.77 kg of purified sulfate of compound C was obtained (79.0% on dry base).

The purified sulfate above was mixed with 15 L of 50% ethanol and neutralized with 25% aqueous ammonia to pH 3.0~3.5. The mixture was filtered, and the cake was washed sufficiently with hot purified water, ethanol and hot purified water again. Then 9.96 kg of purified wet product was obtained (58.5% on dry base), which was dried at 55-65° C.

under at least 0.085 Mpa vacuum for about 24 hours until the Loss on Drying was not more than 0.1%. Finally, 5.48 kg of 2-hydroxy-5-[2-(4-trifluoromethylphenyl)ethylamino]benzoic acid was obtained (99.6% HPLC purity) and the yield was 84.7%.

Analysis of the Final Product $^1$H-NMR spectrum analysis result and IR absorption spectrum analysis result of obtained 2-hydroxy-5-[2-(4-trifluoromethylphenyl)ethylamino]benzoic acid was shown in table 1 and 2, respectively, below.

TABLE 1

| Chemical Shift (ppm) | Multiplicity | Quantity of Proton |
|---|---|---|
| 2.91 | t | 2 |
| 3.23 | t | 2 |
| 6.77 | d | 2 |
| 6.87 | d | 2 |
| 6.96 | s | 1 |
| 7.49 | d | 2 |
| 7.64 | d | 2 |

TABLE 2

| Absorption |
|---|
| IR (cm$^{-1}$, KBr): 3402 (OH), 3070 (Aromatic C—H), 2964, 2916, 2856 (CH$_2$), 2741, 2696, 2536, 2486 (CH$_2$—NH$_2^+$), 1622 (C=O), 1508, 1460 (Aromatic C=C), 1164, 1066 (C—O), 1331, 1113 (C—F), 835, 817 (aromatic ring 1,4-disubstituted), 690 (aromatic ring 1,3,5-trisubstituted) |

ADVANTAGEOUS EFFECTS

The present invention provides a useful and efficient method for mass-producing 2-hydroxy-5-phenylalkylaminobenzoic acid or its salt, particularly 2-hydroxy-5-[2-(4-trifluoromethylphenyl)ethylamino]benzoic acid or its salt.

What is claimed is:

1. A method for preparing 2-hydroxy-5-phenylalkylaminobenzoic acid derivative represented by Chemical formula 4 or its salt at a purity of at least 99%, comprising a step of preparing alkyl 2-hydroxy-5-phenylalkylaminobenzoate represented by Chemical formula 3 by reacting phenylalkyl methanesulfonate represented by Chemical formula 1 with alkyl 5-aminosalicylate represented by Chemical formula 2:

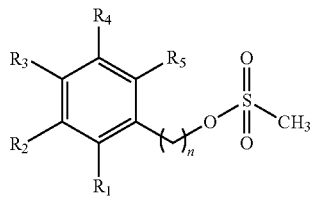

<Chemical formula 1>

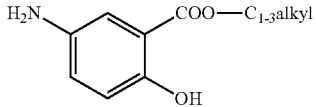

<Chemical formula 2>

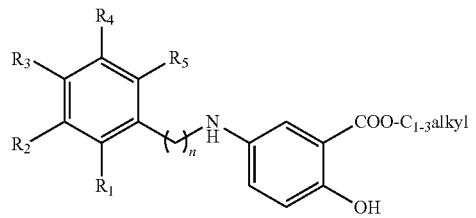

<Chemical formula 3>

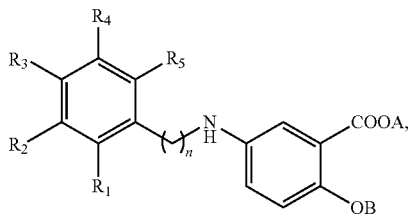

<Chemical formula 4> wherein in the Chemical formulas 1 to 4, n is an integer from 2 to 4; $R_1$, $R_2$, $R_4$ and $R_5$ are hydrogen; $R_3$ is independently hydrogen, halogen, $C_{1-4}$ haloalkyl, nitro, hydroxy, $C_{1-4}$ alkyl, aryl, $C_{1-4}$ alkoxy or amine; A is hydrogen or $C_{1-3}$ alkyl; and B is hydrogen or acetyl;

wherein the method comprises hydrolyzing alkyl 2-hydroxy-5-phenylalkylaminobenzoate represented by Chemical formula 3 to form 2-hydroxy-5-phenylalkylaminobenzoic acid sulfate;

wherein the method comprises controlling the pH of the 2-hydroxy-5-phenylalkylaminobenzoic acid sulfate for purification; and wherein the purity of the 2-hydroxy-5-phenylalkylaminobenzoic acid derivative represented by Chemical formula 4 or its salt is at least 99%.

2. The method of claim 1, wherein the reaction temperature of phenylalkyl methanesulfonate represented by Chemical formula 1 and alkyl 5-aminosalicylate represented by Chemical formula 2 is 60-90° C.

3. The method of claim 1, wherein hydrolyzing alkyl 2-hydroxy-5-phenylalkylaminobenzoate represented by Chemical formula 3 comprises hydrolyzing with a sulphuric acid water solution.

4. The method of claim 1, wherein the pH is 3-3.5.

5. A method for preparing 2-hydroxy-5-[2-(4-trifluoromethylphenyl)ethylamino]benzoic acid represented by Chemical formula 8 at a purity of at least 99%, comprising a step of preparing methyl 2-hydroxy-5-[2-(4-trifluoromethylphenyl)ethylamino]benzoate represented by Chemical formula 7 by reacting 2-(4-trifluoromethylphenyl)ethyl methanesulfonate represented by Chemical formula 5 with methyl 5-aminosalicylate represented by Chemical formula 6:

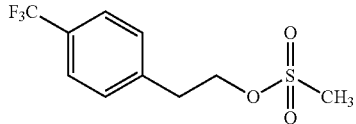

<Chemical formula 5>

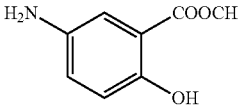

<Chemical formula 6>

<Chemical formula 7>

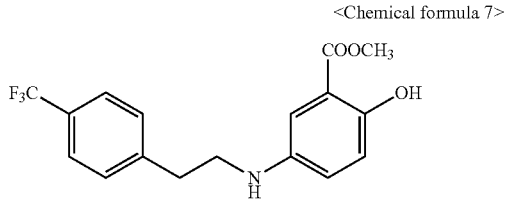

<Chemical formula 8>

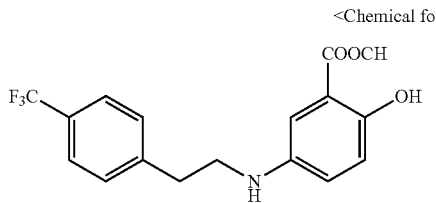

wherein the method comprises hydrolyzing methyl 2-hydroxy-5-[2-(4-trifluoromethylphenyl)ethylamino]benzoate to form 2-hydroxy-5-[2-(4-trifluoromethylphenyl)ethylamino]benzoic acid sulfate;

wherein the method comprises controlling the pH of the 2-hydroxy-5-[2-(4-trifluoromethylphenyl)ethylamino]benzoic acid sulfate for purification; and wherein the purity of the 2-hydroxy-5-[2-(4-trifluoromethylphenyl)ethylamino]benzoic acid represented by Chemical formula 8 is at least 99%.

6. The method of claim 5, wherein the reaction temperature of 2-(4-trifluoromethylphenyl)ethyl methanesulfonate and methyl 5-aminosalicylate is 70-80° C.

7. The method of claim 5, wherein hydrolyzing alkyl 2-hydroxy-5-phenylalkylaminobenzoate represented by Chemical formula 3 comprises hydrolyzing with a sulphuric acid water solution.

8. The method of claim 5, wherein the pH is 3-3.5 for purification.

* * * * *